United States Patent
Schroeder et al.

(10) Patent No.: US 10,633,624 B2
(45) Date of Patent: Apr. 28, 2020

(54) METHODS AND APPARATUS FOR PERFUSION AND ENVIRONMENT CONTROL OF MICROPLATE LABWARE

(71) Applicants: ESSEN INSTRUMENTS, INC., Ann Arbor, MI (US); NATIONAL RESEARCH COUNCIL OF CANADA, Ottawa, Ontario (CA)

(72) Inventors: Kirk S. Schroeder, Ann Arbor, MI (US); Bradley D. Neagle, Ann Arbor, MI (US); Eric Endsley, Saline, MI (US); Daniel Appledorn, Ann Arbor, MI (US); Keith Morton, St Bruno (CA)

(73) Assignees: ESSEN INSTRUMENTS, INC., Ann Arbor, MI (US); NATIONAL RESEARCH COUNCIL OF CANADA, Ottawa (CA)

( * ) Notice: Subject to any disclaimer, the term of this patent is extended or adjusted under 35 U.S.C. 154(b) by 0 days.

(21) Appl. No.: 16/458,863

(22) Filed: Jul. 1, 2019

(65) Prior Publication Data
US 2019/0322972 A1 Oct. 24, 2019

Related U.S. Application Data

(63) Continuation of application No. PCT/US2018/014447, filed on Jan. 19, 2018.
(Continued)

(51) Int. Cl.
*C12M 3/06* (2006.01)
*C12M 1/32* (2006.01)
(Continued)

(52) U.S. Cl.
CPC ............ *C12M 23/16* (2013.01); *C12M 23/12* (2013.01); *C12M 23/20* (2013.01); *C12M 23/38* (2013.01);
(Continued)

(58) Field of Classification Search
CPC ...... C12M 23/16; C12M 23/12; C12M 23/38; C12M 23/20; C12M 29/10; C12M 41/40
See application file for complete search history.

(56) References Cited

U.S. PATENT DOCUMENTS

| | | | |
|---|---|---|---|
| 6,908,767 B2 * | 6/2005 | Bader | B01L 3/5025 435/286.1 |
| 2010/0029000 A1 | 2/2010 | Zhong et al. | |
| 2016/0136646 A1 | 5/2016 | Ingber et al. | |

FOREIGN PATENT DOCUMENTS

| | | |
|---|---|---|
| DE | 40 35 597 | 5/1992 |
| DE | 101 18 905 | 10/2002 |

(Continued)

OTHER PUBLICATIONS

The International Search Report (ISR) with Written Opinion for PCT/US2018/014447 dated Aug. 1, 2018, pp. 1-17.

*Primary Examiner* — Michael L Hobbs
(74) *Attorney, Agent, or Firm* — McDonnell Boehnen Hulbert & Berghoff LLP

(57) ABSTRACT

Systems, methods, and apparatuses of controlling fluid flow are disclosed. An apparatus includes a first microplate having a first open portion and defining one or more first wells therein, a second microplate having a second open portion and defining one or more second wells therein, and a pneumatic lid constructed of styrene ethylene butylene styrene (SEBS). The pneumatic lid extends over the first open portion and the second open portion and includes one or more microfluidic channels that fluidly couple the one or more first wells to the one or more second wells. The (Continued)

pneumatic lid provides an airtight seal over the first microplate and the second microplate.

27 Claims, 7 Drawing Sheets

Related U.S. Application Data

(60) Provisional application No. 62/447,991, filed on Jan. 19, 2017.

(51) Int. Cl.
  *C12M 1/00* (2006.01)
  *C12M 1/12* (2006.01)
  *C12M 1/34* (2006.01)

(52) U.S. Cl.
  CPC ............ *C12M 29/10* (2013.01); *C12M 37/04* (2013.01); *C12M 41/40* (2013.01)

(56) References Cited

FOREIGN PATENT DOCUMENTS

| | | |
|---|---|---|
| DE | 10 2008 008256 | 4/2009 |
| FR | 2 957 087 | 9/2011 |
| WO | 2002/24861 | 3/2002 |
| WO | 2003/064990 | 8/2003 |
| WO | 2015/091928 | 6/2015 |

* cited by examiner

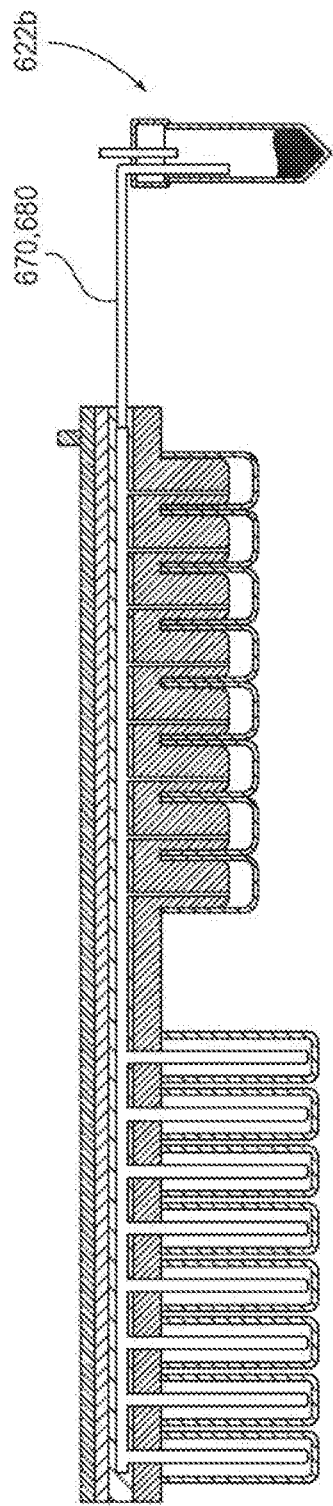
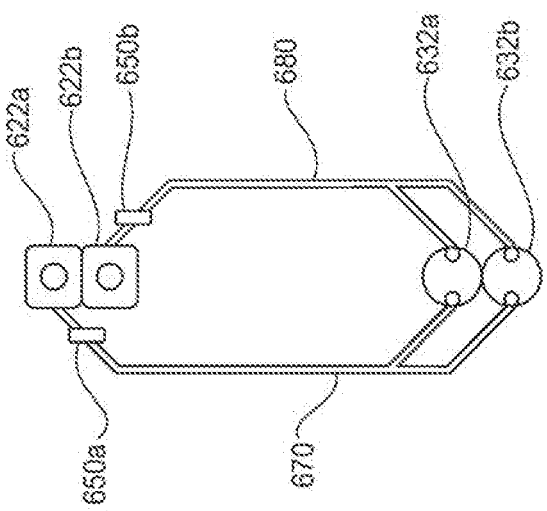
FIG. 6A
FIG. 6B

METHODS AND APPARATUS FOR PERFUSION AND ENVIRONMENT CONTROL OF MICROPLATE LABWARE

CROSS-REFERENCE TO RELATED APPLICATION

This application is a continuation of International Application No. PCT/US2018/014447, filed on Jan. 19, 2018, which claims priority to U.S. Provisional Application No. 62/447,991, filed Jan. 19, 2017, both of which are incorporated by reference herein in their entirety.

TECHNICAL FIELD

The present specification generally relates to enhanced in vitro cell culture, and more particularly, to systems, apparatuses, and methods for providing integrated perfusion and atmospheric control of microplate labware.

BACKGROUND

Currently, many in vitro cell culture techniques exist to provide a method to keep biological cells alive ex vivo over extended time periods. For example, certain techniques include a static culture, manual batch feed in which cells are seeded on a cell culture vessel suspended in media and placed in a temperature- and $CO_2$-controlled incubator. However, such techniques are not ideal for mimicking a true in vivo physiological microenvironment. For example, in a mammalian body, the cellular microenvironment varies considerably from the conditions that can be stimulated in vivo. Therefore, because cells tend to be a product of their microenvironment, the in vivo cultured cells are not a true representative of cells that occur in a physiological environment.

Some solutions to this issue require specialized labware, which is expensive, not commercially available, and/or is particularly suited only for certain applications. Such solutions cannot utilize standard microplate labware, which is widely available for a multitude of laboratory applications. In addition, other solutions are not accessible to light microscopy, contain a limited throughput, contain a limited number of cell wells/chambers (e.g. <12 per microplate footprint), are difficult to handle and/or load cells, lack atmospheric control, lack an ability to control a flow rate, have transient flow rates, have a limited flow duration, have a requirement for re-circulation, have a requirement for mechanical tilting of the plate to extend the duration, and/or do not have independent well control (i.e., all wells undergo identical perfusion treatment).

Accordingly, there exists a continuing need for an in vitro cell culture technique that allows for enhanced control of the cellular microenvironment using standard microplate labware, as well as systems, apparatuses, and the like for carrying out the technique while also being able to integrate with standard microplate labware.

SUMMARY

In an embodiment, a pneumatic lid includes a body having one or more microfluidic channels. At least a portion of the body is constructed of styrene ethylene butylene styrene (SEBS). The pneumatic lid further includes one or more first extension pieces fluidly coupled to the one or more microfluidic channels and extending from the body and one or more second extension pieces fluidly coupled to the one or more microfluidic channels and extending from the body.

In another embodiment, a pneumatic lid includes a first portion having one or more first microfluidic channels that are configured to be fluidly coupled to one or more first wells, a second portion having one or more second microfluidic channels that are configured to be fluidly coupled to one or more second wells that are separate from the one or more first wells, and a removable bridge portion extending between the first portion and the second portion. The removable bridge portion, when coupled to the first portion and the second portion, fluidly couples the one or more first microfluidic channels to the one or more second microfluidic channels. The first portion and the second portion, when coupled to the one or more first wells and the one or more second wells, respectively provide an airtight seal over the one or more first wells and the one or more second wells.

In yet another embodiment, an apparatus includes a first microplate having a first open portion and defining one or more first wells therein, a second microplate having a second open portion and defining one or more second wells therein, and a pneumatic lid constructed of styrene ethylene butylene styrene (SEBS). The pneumatic lid extends over the first open portion and the second open portion and includes one or more microfluidic channels that fluidly couple the one or more first wells to the one or more second wells. The pneumatic lid provides an airtight seal over the first microplate and the second microplate.

In yet another embodiment, an apparatus includes a first microplate having a first open portion and defining one or more first wells therein, a second microplate having a second open portion and defining one or more second wells therein, and a pneumatic lid extending over the first open portion and the second open portion. The pneumatic lid includes one or more microfluidic channels that fluidly couple the one or more first wells to the one or more second wells. The pneumatic lid provides an airtight seal over the first microplate and the second microplate.

In yet another embodiment, an apparatus includes a first microplate having a first open portion and defining one or more first wells therein, a second microplate having a second open portion and defining one or more second wells therein, and a pneumatic lid. The pneumatic lid includes a first portion extending over the first open portion, the first portion having one or more first microfluidic channels that are fluidly coupled to the one or more first wells. The pneumatic lid further includes a second portion extending over the second open portion, the second portion having one or more second microfluidic channels that are fluidly coupled to the one or more second wells. The pneumatic lid also includes a removable bridge portion extending between the first portion and the second portion. The removable bridge portion, when coupled to the first portion and the second portion, fluidly couples the one or more first microfluidic channels to the one or more second microfluidic channels. The pneumatic lid provides an airtight seal over the first microplate and the second microplate.

In yet another embodiment, a method of constructing an apparatus for transferring fluid includes providing a first microplate having a first open portion and defining one or more first wells therein, providing a second microplate having a second open portion and defining one or more second wells therein, and placing a pneumatic lid constructed of styrene ethylene butylene styrene (SEBS) over the first open portion and the second open portion such that one or more microfluidic channels within the pneumatic lid are fluidly coupled to the one or more first wells and the one or more second wells. The pneumatic lid provides an airtight seal over the first microplate and the second microplate.

In yet another embodiment, a method of constructing an apparatus for transferring fluid includes providing a first microplate having a first open portion and defining one or more first wells therein, providing a second microplate having a second open portion and defining one or more second wells therein, placing a first portion of a pneumatic lid over the first open portion such that one or more first microfluidic channels within the first portion are fluidly coupled to the one or more first wells, placing a second portion of a pneumatic lid over the second open portion such that one or more second microfluidic channels within the second portion are fluidly coupled to the one or more second wells, and placing a removable bridge portion between the first portion and the second portion of the pneumatic lid to fluidly couple the one or more first microfluidic channels to the one or more second microfluidic channels.

In yet another embodiment, a system for transferring fluid includes a first microplate having a first open portion and defining one or more first wells therein, a second microplate that is separate front the first microplate the second microplate having a second open portion and defining one or more second wells therein, a pneumatic lid, and one or more valves. The pneumatic lid is constructed of styrene ethylene butylene styrene (SEBS) which forms a reversible and gas impermeable bond with the first microplate and the second microplate. The pneumatic lid includes a first portion extending over the first open portion, the first portion including one or more first extension pieces extending into the one or more first wells of the first microplate and one or more first microfluidic channels that are fluidly coupled to the one or more first wells via the one or more first extension pieces, a second portion extending over the second open portion, the second portion including one or more second extension pieces extending into the one or more second wells of the second microplate and one or more second microfluidic channels that are fluidly coupled to the one or more second wells via the one or more second microfluidic channels, and a removable bridge portion extending between the first portion and the second portion. The removable bridge portion, when coupled to the first portion and the second portion, fluidly couples the one or more first microfluidic channels to the one or more second microfluidic channels. The one or more valves are fluidly coupled to the pneumatic lid and configured to selectively control fluid flow within the one or more first microfluidic channels and the one or more second microfluidic channels. The fluid is transferred between the first microplate and the second microplate via the pneumatic lid and the one or more valves.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, wherein like structure is indicated with like reference numerals and in which:

FIG. 6A depicts a schematic view of an illustrative apparatus for waste collection according to one or more embodiments shown and described herein; and FIG. 6B depicts a schematic view of an illustrative pneumatic lid interface well mapping interface for waste collection according to one or more embodiments shown and described herein.

DETAILED DESCRIPTION

Figure 1A:
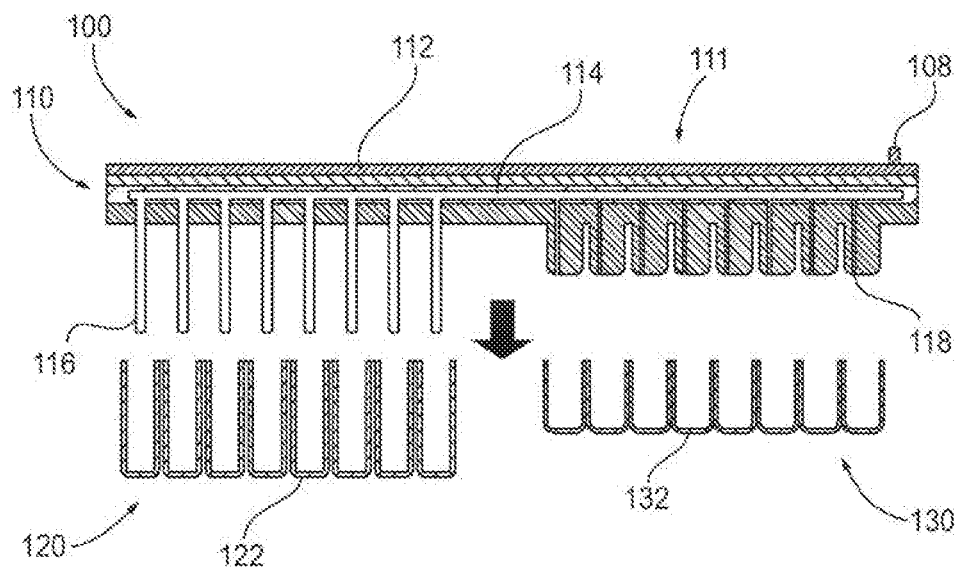
FIG. 1A depicts an exploded schematic cross-sectional view of an illustrative apparatus for providing integrated perfusion and atmospheric control of microplate labware according to one or more embodiments shown and described herein.

Referring generally to the figures, embodiments described herein are directed to in vitro cell culture techniques that utilize methods, systems, and apparatuses to provide control of a cellular microenvironment using standard microplate labware by providing a device with a large well throughput, atmospheric control, active fluid perfusion of any and all wells, extended experimental perfusion duration, and compatibility with simultaneous microscopic imaging. The embodiments described herein generally include a plurality of microplates that are fluidly joined together via a pneumatic lid that is at least partially constructed of a thermoplastic elastomer that forms a reversible and gas impermeable bond with the plurality of microplates. More particularly, the thermoplastic elastomer is or includes styrene ethylene butylene styrene (SEBS).

As used herein, the terms "microplate labware" or "standard microplate labware" refer to labware that is generally understood and used for the purposes of cell culture, particularly mammalian cell culture. Illustrative examples of such labware include, but are not limited to, open culture labware vessels such as microplates, T-flasks, petri dishes, or the like, particularly vessels that are suited for batch-feed processes.

The various techniques of the present disclosure may include certain in vitro cell culture techniques that keep biological cells alive ex vivo over extended time periods. Illustrative techniques may include, for example, cell culture vessels generally fabricated from injection molded plastic including multi-well plates, T-flasks, petri dishes, or the like. Such cell culture vessels may be configured to breathe, i.e., the internal gas concentrations are intended to equilibrate to the gaseous environment in which they are placed. Certain design features described herein may filter this gas exchange in an attempt to eliminate air-borne contaminants such as bacteria or fungal spores. Specialized media, supplements, and saline solutions customized to the biology under study may be used with a prime objective of providing the essential basic salts, amino acids, nutrients, and growth factors for the purpose of keeping cells healthy. In addition, the methods, systems, and apparatuses described herein may include maintenance of physiological temperatures (e.g., about 37° C.), maintenance of physiological pH by using, for example, bicarbonate buffered solutions and a specific partial pressure of carbon dioxide (e.g., about 5%), and/or maintenance in a humidified environment, such as, for example, an environment having a relative humidity of about 90 to about 95%. Such a humidified environment may be necessary to reduce evaporation of fluid in the lab culture vessels. Such evaporation could potentially result in adverse changes in osmolarity of the solution, which may cause harmful effects to the cells.

Certain cell feeding techniques, such as a technique that involves a static culture, manual batch feed, cells may be seeded on a cell culture vessel suspended in media and placed into a temperature controlled incubator for temperature and $CO_2$ maintenance, as described herein. Adherent cells may fall to the bottom of the vessel and may subsequently attach to the cell surface. Non-adherent cell types may be cultured in this manner, or may be cultured in Spinner-Flasks that maintain the cells in suspension via constant stirring. To minimize human intervention, the media may carry an excess of nutrient constituents such that the cells remain viable for a particular time period, such as, for example, at least about 24 hours from the initial feeding. During this time, nutrients may be consumed by the cells and waste products may be generated. Once the nutrients have been consumed and/or the waste products have built up to levels which can affect the cells health directly, a user may remove the vessel from the incubator and replace all or a portion of the cell media, use the cells in an experiment, or harvest the cells for further uses or seeding of new vessels. It should be understood that such cellular manipulation (feeding, harvesting, or passaging) may be performed within a sterile biological cabinet at typical atmospheric conditions and at room temperature.

Such cell feeding techniques may not mimic the in vivo physiological microenvironment. This is because, in vivo, tissues obtain a steady state supply of nutrients as fed by the arterial system (source) and drained by the venous and lymphatic systems (sinks). The actual interstitial flows (tissue flow) which feed cells are tissue dependent and based on the local metabolic demands of the tissue. This tissue dependence is accommodated by the arterial spacing (higher metabolic demand tissues have closer capillary spacing), pressure differentials dominated by local hydrostatic and osmotic pressure differences between the capillaries/venuoles and the tissue, and the fluid permeability of the local tissue environment. Interstitial flows are typically quite small, on the order of tens of microns per minute, and as such, the flow of nutrients and waste removal is a slow, steady-state concentration of nutrients and waste products.

Use of such cell feeding techniques may result in cells that are a product of their cultured microenvironment, and vice-versa. For example, cell metabolism of cells in a cultured microenvironment may differ from cells that occur naturally in vivo. Cellular catabolic metabolism can shift from glycolysis (glucose input) to oxidative phosphorylation (pyruvate and oxygen) to glutaminolysis (glutamine input) depending on the availability of such nutrients. In addition, organisms can adapt to transient supply/demand variations by storing away fuel via glycogen storage, fatty acid anabolism or the Pentose Phosphate Pathway or call upon fuel stores via lipolysis and fatty acid catabolism. Typical waste products such as lacate may become sources of fuel under certain conditions. In contrast, cell culture media may supply about 3 to about 10 times excess concentrations of these fuel sources in order to keep cells viable for multiple days. In addition, cell culture media may contain excess levels of amino acids and vitamins in much the same manner. Such cell culture media may also be optimized such that the cell culture media is broadly applicable to many cell types. Moreover, batch-feed processes may be optimized for convenience, such as, for example, requiring manually feeding only every few days.

Similarly, the cultured cells can have an effect on the local microenvironment. Cells may secrete waste products, growth factors, cytokines, and other signaling molecules. Some secreted products may have an impact on the cells that secreted the products or on other cells via autocrine or paracrine signaling. If such secreted products are allowed to build up within a static, batch feed feeding process, concentration gradients and transients form, which may not be representative of the in vivo condition in which a steady flow removes waste products in a more stable, homeostatic condition.

In addition, some tissues in the body have oxygen concentrations which are less than atmosphere concentrations (e.g., about 21%). For example, typical concentrations in the liver are about 3% to about 9% and in the brain are about 2% to about 7%, and an actual concentration may form a decreasing concentration gradient in tissues that are located farther away from a supply capillary. Since oxygen is a necessary input to mammalian cell metabolism via the citric acid cycle or the Krebs cycle, changes in an available oxygen concentration may have an effect on cell phenotype.

Various cell culture techniques may require a manual intervention to feed cells, which may be time consuming and may contaminate the cells and/or the media. Microplates may be configured to breathe by exchanging air around the perimeter of the microplate. However this may create a non-uniform air flow and may cause greater evaporation around the edge wells of the microplate, relative to the center wells of the plate. Such a non-uniform evaporation may cause osmolarity differences and edge effects on microplate cell cultures.

Some cell culture devices may incorporate integrated perfusion, such as microfluidic cell culture devices that incorporate microfluidic cell chambers with integrated channels and valving. Illustrative microfluidic features generally include design elements having feature dimensions on the order of tens to hundreds of microns. However, microfluidic devices have not been commercially viable because such devices are much different to work with than standard microplate, or "open vessel" labware vessels. This is because seeding a cell in a microfluidic cell culture device may often be done by microinjection via a hypodermic needle device or connection, which is more difficult for the user and harder to standardize than traditional open-vessel cell culture where multi-channel pipetors or robotics are used. In addition, some microfluidic devices are composed of materials such as polydimethylsiloxane (PDMS) because such materials are amenable to prototype microfabrication and are bio-inert. However, PDMS micro-fabrication is difficult to mass produce. PDMS is also highly adsorbent of lipophilic compounds, which presents problems for drug screening applications where such lipophilic compounds are common. Furthermore, PDMS breathes, which presents a design complication for applications requiring atmospheric control. In addition, interfacing to such devices may be problematic, particularly for placing experimental drugs traditionally stored in robotic compatible microplate devices into microfluidic structures. As such, microfluidic devices may only be available for certain applications such as protein crystallization, protein analysis, and PCR, but are not suited for cell analysis.

"Tissue on a chip" or "organ on a chip" applications are generally not suited for in vitro cell culture as described herein because such applications lack inherent atmospheric control, low test chamber throughput, and require recirculation of media instead of removing waste media. In addition, the cell chamber in such applications is inaccessible to integrated microscopy. Moreover, fluid perfusion of all sample bioreactors must occur in parallel.

Microfluidic cell culture devices that use a single standard "microplate-like" device having microfluidic channels that are incorporated into the device in order to move fluids from individual wells to specially constructed microfluidic cell chambers also built on the device and use a pneumatic manifold to hermetically seal to the top of the plate to apply pneumatic pressure are also not suited for in vitro cell culture as described herein. This is because the design includes a low throughput, as there are few cell culture chambers (e.g., four chambers) per plate. In addition, a passive gravity flow method as implemented in such a design is inherently transient and defined by the ever-changing fluid height difference between source and waste wells. As such, a user has no control of flow initiation or flow rate, which limits a duration of experimentation, as the fluid volume of the source wells are quickly expended. This, in turn, drives the need to attach many source wells to a given cell chamber, thereby expanding experiment duration but limiting available cell chamber number for a given lab vessel footprint. Other techniques to increase flow duration time include adding mechanical interventions, such as tilting the plate to mechanically manipulate fluid height differences between source and sink wells and thereby increase flow duration time, resulting in a reversal of the flow direction.

Devices that incorporate specially designed cell culture vessels mated to a fluid transfer base plate that is controlled by a computer are also not suited for in vitro cell culture as described herein because such device's use non-traditional cell culture labware. Similarly, devices that are a hybrid, between traditional microplate culture, plates and microfluidic cell culture, plates, use a pneumatic pressure driven lid that mates with, a traditional 24-well microplate, and moves fluid is from different wells of the microplate through integrated capillary tubes via a system of integrated valving and precisely timed air pressure and vacuum application are also not suited for in vitro cell culture as described herein. This is because such devices suffer from low throughput, use of only six measurement wells, requires perfusion of all wells simultaneously, and the valving components utilize a flexible PDMS layer to open and close the micro-channels, which, as previously described herein, is absorbent of lipophilic compounds and is permeable to gases, which are not controlled.

Figure 1B:
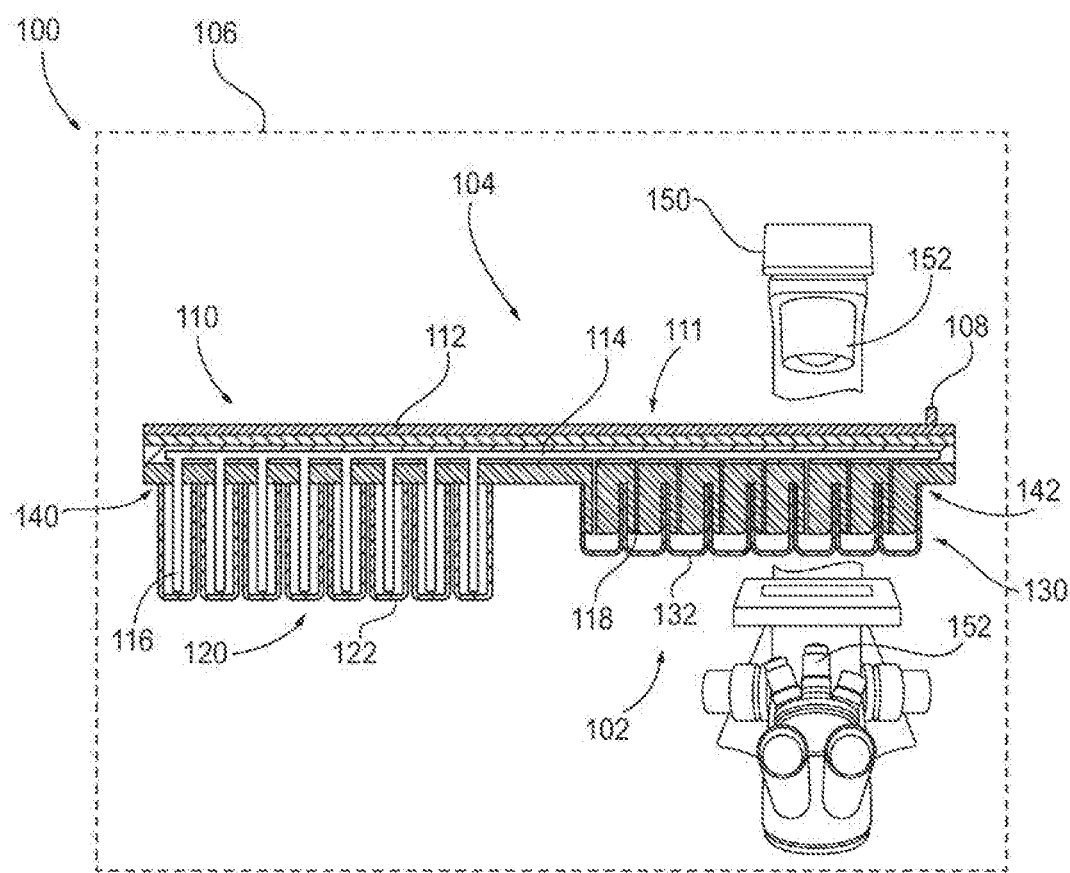
FIG. 1B depicts a schematic cross-sectional view of an illustrative apparatus for providing integrated perfusion and atmospheric control of microplate labware when coupled to the microplate labware according to one or more embodiments shown and described herein.

Referring now to the drawings, FIGS. 1A and 1B depict schematic views of an illustrative apparatus, generally designated 100, for providing integrated perfusion and atmospheric control of microplate labware. More specifically, FIG. 1A depicts the various components of the apparatus 100 in an exploded schematic view and FIG. 1B depicts the various components of the apparatus 100 when assembled, as described in greater detail herein. In some embodiments, the apparatus 100 is housed within a temperature controlled environment 106, such as an incubator or the like.

As particularly shown in FIG. 1B, the apparatus 100 may be positioned such that a bottom portion 102 thereof can be imaged via a microscope objective 154 of the microscope 150 and a corresponding top portion 104 thereof is adjacent to a lamp housing 152 of the microscope 150. As such, the materials used for constructing various components of the apparatus 100 are sufficiently transparent so to allow light from the lamp housing 152 to illuminate the cells within the various wells 132. Accordingly, the apparatus 100 may be compatible with phase contrast or other transmissive light microscopy techniques. In some embodiments, the apparatus 100 may also be compatible with epi-fluorescence imaging devices with excitation light entering the microscope objective from the bottom portion 102 of the apparatus 100.

Still referring to FIGS. 1A and 1B, the apparatus 100 generally includes a pneumatic lid 110 that is placed on various types of microplate labware, including, but net limited to, a deep well source microplate 120 and a cell assay microplate 130. The pneumatic lid 110 may be placed on an opening of the various microplate labware so as to seal the microplate labware from an outside environment and/or to secure the pneumatic lid 110 to the microplate labware, as described in greater detail herein.

The pneumatic lid 110 may be, for example, a specially designed, sterile, pneumatic lid consumable. The pneumatic lid 110 includes a body 111 having one or more pneumatic control fittings 108, one or more first extension pieces 116, one or more second extension pieces 118, and one or more microfluidic channels 114 fluidly coupling the one or more first extension pieces 116 with the one or more second extension pieces 118. The one or more microfluidic channels 114 may generally provide perfusion capabilities between the various microplate labware via the one or more first extension pieces 116 and/or the one or more second extension pieces 118. For example, when the apparatus 100 is assembled as shown in FIG. 1B, the first extension pieces 116 may extend into the deep well source microplate 120 and the one or more second extension pieces 118 may extend into the cell assay microplate 130. As such, in order to increase the capacity of the apparatus 100 and yet not limit the number of cell culture wells per device, the pneumatic lid 110 may provide a bridge between two or more microplates, such as the deep well source microplate 120 and the cell assay microplate 130, as depicted in FIG. 1B.

The pneumatic lid 110 may be constructed of any material, and is otherwise not limited by this disclosure. In some embodiments, the pneumatic lid 110 may be constructed of a plurality of layers of material. For example, the pneumatic lid may have a top layer 112 over a middle layer comprising the microfluidic channels 114. In some embodiments, the pneumatic lid 110 may be constructed of materials that do not incorporate PDMS. In such embodiments, the materials may be more compatible with the transfer of lipophilic drugs relative to materials that do incorporate PDMS. In addition, unlike PDMS, the materials used in construction of the pneumatic lid 110 are not permeable to gases at least to the extent that a gas composition of supplied air remains substantially unaltered. In some embodiments, the pneumatic lid 110 or a portion thereof (e.g., a portion of the body 111) may be constructed of a thermoplastic elastomer (such as styrene ethylene butylene styrene (SEBS)) to make a reversible, yet gas impermeable, bond with the microplates. SEBS is a thermoplastic elastomer (TPE) comprised of a mixture of hard polymer such as polystyrene with ethylene-butylene chains. The ethylene-butylene chains give the material its flexibility and the percentage composition of the hard polymer composition can be customized depending on the desired characteristics required. The more polystyrene used in the mix, the harder the material and the more chemically inert. The less polystyrene used in the mix, the softer the material and the less chemically inert. The advantages of SEBS over other compounds such as PDMS is that SEBS is less absorbent to lipophilic compounds and can easily and reversibly be bonded to glass, polystyrene, or itself without using solvents. SEBS compounds may also be less gag permeable than other compounds such as PDMS, which may be preferable when building an environmentally closed system as described herein. As such, SEBS may be more desirable than other compounds in some embodiments. Depending on the polystyrene composition, the material can be injection molded or hot embossed.

The closed system as described herein may allow for atmospheric control and may eliminate various long term evaporation, and specifically non-uniform evaporation, between the center wells and the edge wells of a particular microplate. This type of evaporation may be common in other microplate lid designs which non-uniformly exchange air with an incubator environment. This air exchange and subsequent non-uniform evaporation can cause temperature variations as well as osmolarity changes producing edge effects predominant in other microplate lid designs.

In some embodiments, the pneumatic lid 110 may be devoid of mechanical means, such as damps, pins, screws, or the like, for securing the pneumatic lid 110 to the microplate labware. Rather, the pneumatic lid 110 may be secured to the microplate labware via any other non-mechanical means, such as, for example, via vacuum pressure or via use of certain materials described herein. Use of non-mechanical means to secure the pneumatic lid 110 to the microplate labware may be advantageous over use of mechanical means because some mechanical means are not reversible. As such, a user would not be able to remove the lid and reattach it to the same or other microplate labware.

Figure 1C:
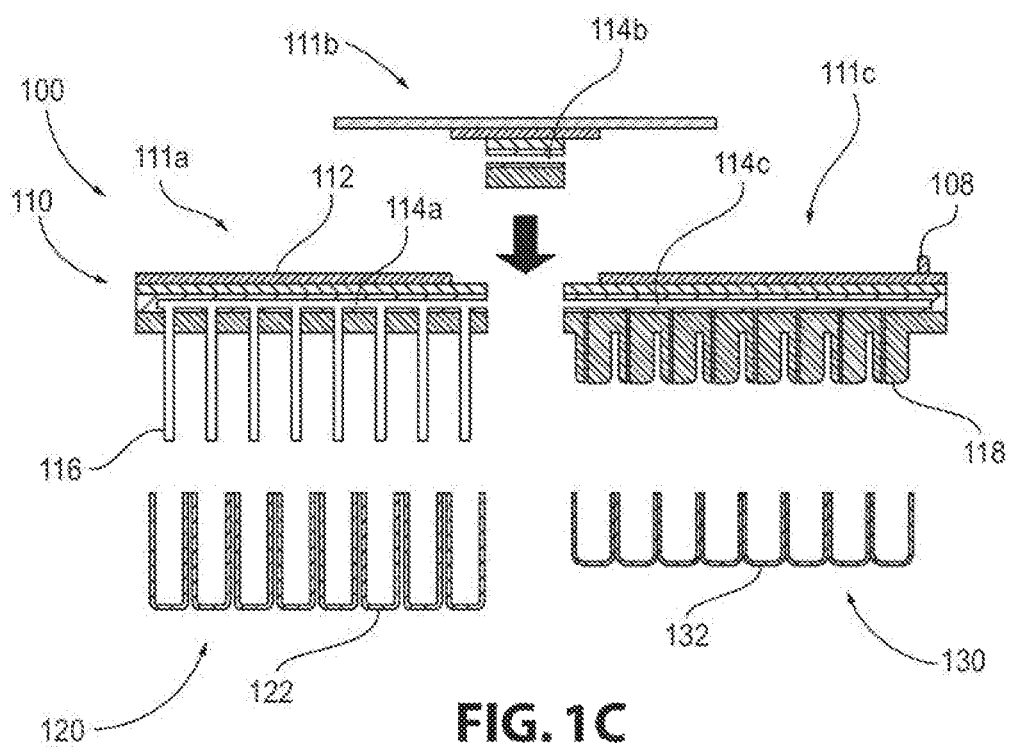
FIG. 1C depicts an exploded schematic cross-sectional view of an illustrative apparatus having a bridge portion, the apparatus providing integrated perfusion and atmospheric control of separate microplate labware, according to one or more embodiments shown and described herein.
Figure 1D:
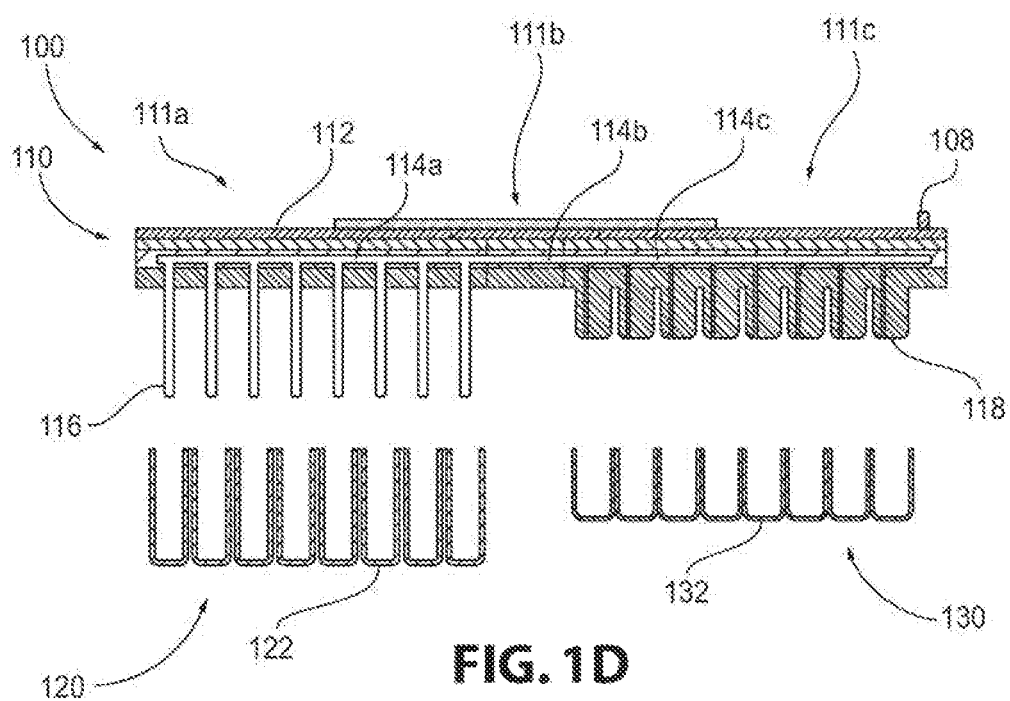
FIG. 1D depicts a schematic cross-sectional view of an illustrative apparatus having a bridge portion when coupled to separate microplate labware according to one or more embodiments shown and described herein.

Referring now to FIGS. 1C and 1D, in some embodiments, the pneumatic lid 110 may have a plurality of portions 111 to facilitate coupling to the microplate labware by allowing each section to be individually coupled to a corresponding microplate labware and then bridged together. For example, the pneumatic lid 110 may include a first portion 111*a* that couples to the deep well source microplate 120, a second portion 111*c* that couples to the cell assay microplate 130 and is separate from the first portion 111*a*, and a bridge portion 111*b* that couples between the first portion 111*a* and the second portion 111*c* to fluidly connect the first portion 111*a* to the second portion 111*c*. As such, the pneumatic lid 110 may allow for a user to individually couple each of the first portion 111*a* and the second portion 111*c* to their respective microplate labware without hindering coupling of the other. Then, once the first portion 111*a* and the second portion 111*c* are coupled, the bridge portion 111*b* is placed between the first portion 111*a* and the second portion 111*c*, as particularly shown in FIG. 1D. Accordingly, the bridge portion 111*b* comprises bridge microfluidic channels 114*b* that align with and fluidly couple to first microfluidic channels 114*a* in the first portion 111*a* and second microfluidic channels 114*c* in the second portion 111*c* so that fluid flow is enabled through the first microfluidic channels 114*a* and the second microfluidic channels 114*c* in a manner as described herein.

Referring again to FIGS. 1A and 1B, the microplate labware is generally standard microplate labware as commonly understood, and is used as a cell culturing device. Use of such microplate labware provides a large degree of familiarity and experimental flexibility with respect to existing cell culture work flow and methods. Illustrative examples of microplate labware that may be used include, but are not limited to, the deep well source microplate 120 and the cell assay microplate 130. The deep well source microplate 120 and the cell assay microplate 130 may be, for example, microplates having a similar format and/or configuration. The deep well source microplate 120 may generally include one or more wells 122 that are configured to contain a reagent. In some embodiments, the deep well source microplate 120 may be particularly configured to increase reagent capacity and total perfusion time for a given flow rate. In some embodiments, the deep well source microplate may have a height of about 1 centimeter (cm) or greater. In various embodiments, the cell assay microplate 130 may contain various cells that are to be studied. The cell assay microplate 130 may be, for example, a microplate that also contains one or more wells 132. In a particular embodiment, the cell assay microplate 130 may be a standard 96-well microplate. However, other types of microplates should generally be understood to be useful in this context and the type of the various microplates is not limited to the present disclosure. However, for the sake of illustration, FIGS. 1A and 1B each depict a 96 well format source and destination plate in a cross-sectional view.

Fluid may move from the one or more wells 122 of the deep well source microplate 120 into the one or more wells 132 of the cell assay microplate 130 via the one or more first extension pieces 116, the microfluidic channels 114 incorporated within the pneumatic lid 110, and/or the one or more second extension pieces 118. More specifically, the microfluidic channels 114 may utilize pneumatic pressure or a vacuum to effect fluid movement between microplates. The pneumatic pressure or the vacuum may be introduced through the one or more pneumatic control fittings 108.

As previously described herein, FIG. 1B depicts the pneumatic lid 110 when engaged with the individual microplates (e.g., the deep well source microplate 120 and the cell assay microplate 130). When the pneumatic lid 110 is engaged with the microplates, an airtight seal 140 is formed between the pneumatic lid 110 and the microplates.

Such a closed (e.g., sealed) system as described herein may be necessary to initiate pressure differentials (positive or negative) so as to move fluids between various components, control the rate of fluid flow, and/or control a duration of fluid flow. For example, the closed system may allow for fluid flow between the one or more wells 122 of the deep well source microplate 120, the one or more wells 132 of the cell assay microplate 130, and/or the microfluidic channels 114 via the one or more first extension pieces 116 and/or the one or more second extension pieces 118. In addition, sealing of the pneumatic lid 110 to the microplates may be necessary in order to maintain the gas composition of the liquid reagents used in the apparatus 100, as described herein.

Figure 2:
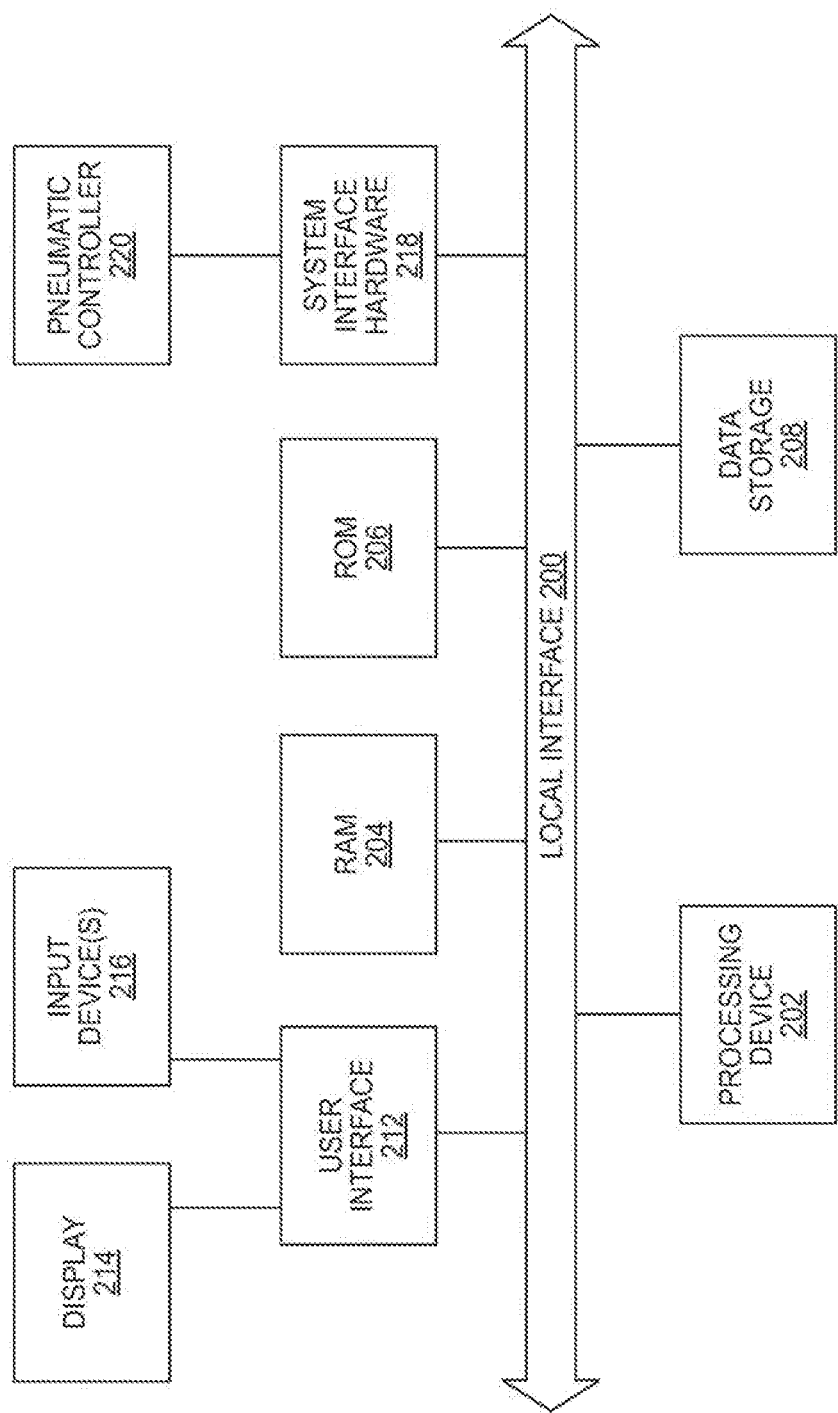
FIG. 2 depicts a block diagram of illustrative hardware that may be used to control an apparatus for providing perfusion and atmospheric control of microplate labware according to one or more embodiments shown and described herein.

Referring also to FIG. 2, the pneumatic pressure or vacuum that is generated to form the airtight seal 140 may be controlled by a pneumatic controller 220 fluidly coupled to the one or more pneumatic control fittings 108. As shown in FIG. 2, the pneumatic controller may generally be a portion of a computing device that is configured to control the pneumatic-pressure and/or vacuum used to move fluids between microplates. The pneumatic controller 220 is configured such that each source well can be activated for flow independently, arbitrary grouped, or all activated simultaneously depending on the application. The pneumatic controller 220 may also be configured to control a gas composition of air that is supplied to the one or more pneumatic control fittings 108. For example, the pneumatic controller 220 may control the oxygen partial pressure of the air supplied to the one or more pneumatic control fittings 108. In some embodiments, the pneumatic controller 220 may allow the pneumatic lid 110 to form the airtight seal 140 with the microplates such that the fluid within the microplates equilibrates to the constituency of the gas supplied. This provides a means of controlling the dissolved oxygen (Or any other dissolved gas) content of the liquid reagents within the apparatus 100.

The various other hardware components, depicted in FIG. 2 may be particularly configured to carry out various tasks for controlling the environment of the microplates once the pneumatic lid 110 has been placed thereover. A local interface 200 (such as a bus) may interconnect the various components. A processing device 202, such as a computer processing unit (CPU) may be the central processing unit of the computing device, performing calculations and logic operations required to execute a program. The processing device 202, alone or in conjunction with one or more of the other elements disclosed in FIG. 2, is an illustrative processing device, computing device, processor, or combination thereof, as such terms are used within this disclosure. Memory, such as read only memory (ROM) 206 and random access memory (RAM) 204, may constitute illustrative memory devices (i.e., non-transitory processor-readable storage media). Such memory 204, 206 may include one or more programming instructions thereon that, when executed by the processing device 202, cause the processing device 202 to complete various processes, such as the processes described herein. Optionally, the program instructions may be stored on a tangible, computer-readable medium such as a compact disc, a digital disk, flash memory, a memory card, a USB drive, an optical disc storage medium, such as a Bluray™ disc, and/or other non-transitory processor-readable storage media.

A data storage device 208, which may generally be a storage medium that is separate from the RAM 204 and the ROM 206, may contain a repository for storing data such as pressure data or the like. The data storage device 208 may be any physical storage medium, including, but not limited to, a hard disk drive (HDD), memory, removable storage, and/or the like. While the data storage device 208 is depicted as a local device, it should be understood that the data storage device 208 may be a remote storage device, such as, for example, a server computing device, cloud based storage, and/or the like.

A user interface 212 may permit information from the local interface 200 to be displayed on a display 214 portion of the computing device in audio, visual, graphic, or alphanumeric format. Moreover, the user interface 212 may also include one or more input devices 216 that allow for transmission to and receipt of data from input devices such as a keyboard, a mouse, a joystick, a touch screen, a remote control, a pointing device, a video input device, an audio input device, a haptic feedback device, and/or the like. Such a user interface 212 may be used, for example, to allow a user to interact with the apparatus 100 to adjust a pressure or the like. For example, a user may interact with the apparatus 100 to provide experimental parameters to ensure that an appropriate environment is created on the microplates.

A system interface 218 may generally provide the computing device with an ability to interface with the pneumatic controller 220 and/or one or more external components. Communication with the pneumatic controller 220 and/or external components may occur using various communication ports (not shown). An illustrative communication port may be attached to a communications network, such as the Internet, an intranet, a local network, a direct connection, and/or the like.

Controlled movement of fluid using pressure (or vacuum) through the apparatus 100 may be accomplished in one or more different manners. For example, in some embodiments, the apparatus 100 may include individual control lines to each source well whereby the fluid flow can be activated by the pneumatic controller to turn on/off the line pressure to each well. This approach may be advantageous because it allows for a pneumatic lid 110 that is lacking any valves, which reduces the complexity of the design of the pneumatic lid 110. Rather, the valves are located within the pneumatic controller 220. Such a design feature may require pressurization and de-pressurization of the entire pneumatic control line and head space above each reservoir well upon each activation.

In some embodiments, the apparatus 100 may incorporate a normally closed integrated valve design, such as, for example, a Quake valve. Such an integrated valve design may rely on a microfluidic channel configuration that is partially comprised of a softer material which can be pushed (pressure) or pulled (vacuum) against a mating valve seat typically of a less flexible material to close or open and thereby turn off or turn on fluid flow in the microfluidic channel. Such valves can be configured as normally open (open unless activated) or normally closed (closed unless activated) depending on the configuration. In some embodiments, the apparatus 100 may incorporate a normally closed valve such that fluid flow does not occur unless actuated by the pneumatic controller 220. In such embodiments, the normally closed valve may incorporate an elastomeric material that is amenable to microfabrication and is also bio-inert.

In some embodiments, SEBS may be used as an elastomeric deflective material for an integrated normally closed valve design. For example, a design that incorporates integrated valves fluidly coupled to channels that are embossed or injection molded SEBS material and mated to a less flexible, material like polystyrene (PS) or cyclin olefin polymer (COP) in completing the channel. In other embodiments, various channel features may be constructed of PS or COC, with valve actuation components constructed of SEBS.

In various embodiments, the polystyrene composition of the SEBS used in the various components of the apparatus 100 may be varied and optimized to address the various requirements. For example, requirements of forming a reversible bond not requiring solvent, a layer that maintains seal in the presence of the pressures required for perfusion function, a bonding layer that is configured for mating to standard microplate labware while maintaining various mechanical tolerances, and a bonding layer which is not permeable to gases for the purpose of maintaining gas composition of the media may be addressed.

Figure 3A:
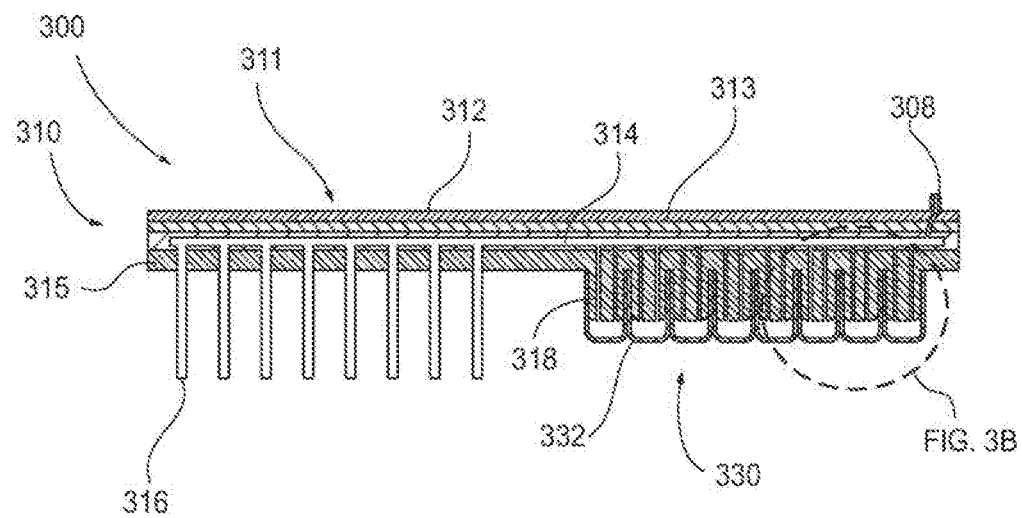
FIG. 3A depicts a schematic view of an illustrative pneumatic lid that incorporates solid polymer plugs at a destination plate interface according to one or more embodiments shown and described herein.

FIG. 3A depicts a schematic view of an illustrative pneumatic lid that incorporates solid polymer plugs at a destination plate interface. In the embodiment depicted in FIG. 3A, a pneumatic lid 310 may include a body 311 having four polymer layers. A top layer 312 of the pneumatic lid 310 is comprised of a harder polymer (polystyrene, cyclic olefin polymer, and/or the like). The top layer 312 may contain one or more pneumatic control fittings 308 that are fluidly coupled to a pneumatic controller (not shown), such as the pneumatic controller 220 (FIG. 2) described hereinabove. In some embodiments, the top layer 312 may contain one or more pneumatic air channels that run spatially across the pneumatic lid 310 for individual valve control and/or well pressurization. The pneumatic lid 310 may further include a second layer 313 underneath the top layer 312. The second layer 313 may be comprised of a thermoplastic elastomer (TPE), such as SEBS or the like. The second layer 313 may be utilized as a deflection layer for an integrated valve design. In some embodiments, the second layer 311 may not contain microfluidic channels (featureless). Rather, the second layer 313 may be mated to a third layer 314 constructed of a polymer and containing embossed or injection molded microfluidic channels therein. In such an arrangement, the second layer 313 may be sandwiched between the top layer 312 and the third layer 314. The microfluidic channels located within the third layer 314 may have lateral dimensions of about 30 microns to several hundred microns. One or more extension pieces extending from the third layer 314 may provide an interface to the individual microplates. For example, in some embodiments, an interface between the microfluidic channels in the third layer 314 and a source plate may include one or more capillary tubes 316. In some embodiments, the one or more capillary tubes 316 may be injection molded as a portion of the third layer 314. In other embodiments, the one or more capillary tubes 316 may be inserted separately into the third layer 314.

Figure 3B:
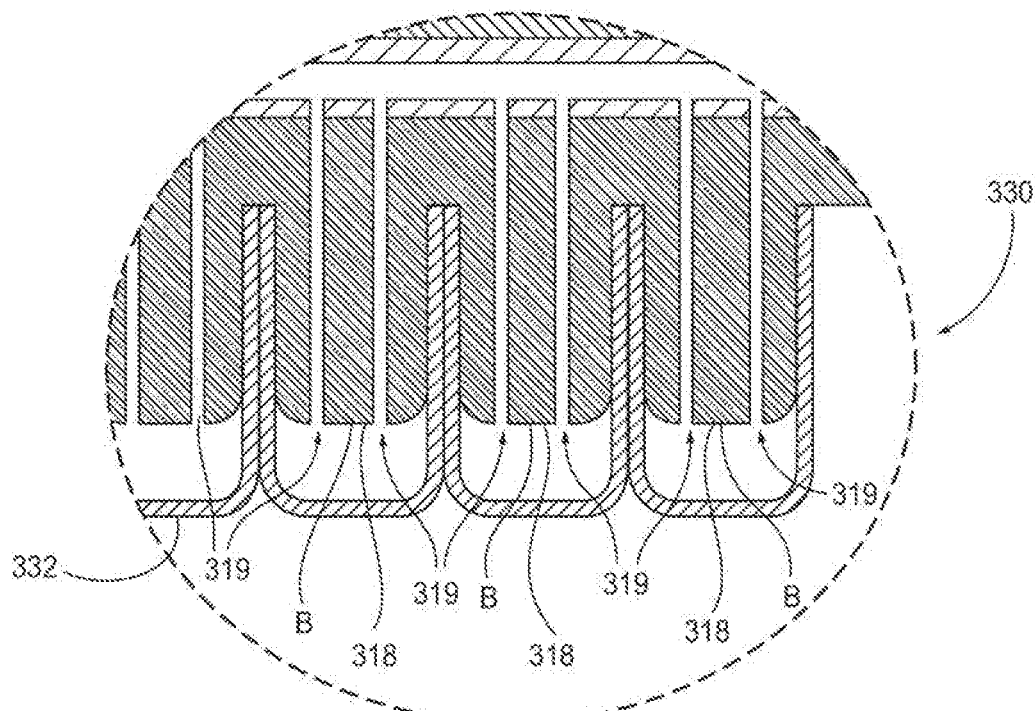
FIG. 3B depicts a detailed view of the solid polymer plugs of FIG. 3A at the destination plate interface according to one or more embodiments shown and described herein.

FIGS. 3A and 3B depict another embodiment where the apparatus, generally designated 300, incorporates a pneumatic lid 310. Except as specifically described herein, the various remaining components shown in FIGS. 3A and 3B may be constructed and configured similar to the like-numbered components in FIGS. 1A and 1B. For example, the top layer 312 depicted in FIG. 3A may be constructed and configured in a manner similar to the top layer 112 described with respect to FIG. 1A.

As shown in FIGS. 3A and 3B, a destination cell plate 330 may have one or more wells 332 that have extension pieces from the third layer 314 inserted therein. Such extension pieces may be, for example, solid polymer plugs 318 that contain one or more bores 319 therein. The one or more bores 319 may function as inlet and/or outlet fluid paths into a respective well 332 of the destination cell plate 330. Use of such plugs 318 may provide an advantage over other apparatuses as fluid levels at the bottom of each well 332 in the destination cell plate 330 can be confined. In addition, use of such plugs 318 may eliminate a meniscus in the fluid contained in each well 332. Elimination of a meniscus may allow for more accurate imaging of the contents of each well 332, as a meniscus may cause artifacts that are detrimental to microscopic imaging. In some embodiments, as particularly shown in FIG. 3B, a bottom portion B of each plug 318 may be particularly shaped and/or sized. Such a particular shape and/or size of the bottom portion B may be generally for the purposes of priming and bubble removal. In addition, the shape and/or size of the bottom portion B may aid in providing an ease of designing and manufacturing of the plug 318.

In some embodiments, the pneumatic lid 310 may also incorporate a fourth layer 315 underneath the third layer 314, such that the third layer 314 is positioned between the second layer 313 and the fourth layer 315. The fourth layer may be comprised of a thermoplastic elastomer, and may generally be used to provide a sealing surface for attachment to the individual microplates as described herein.

Figure 4A:
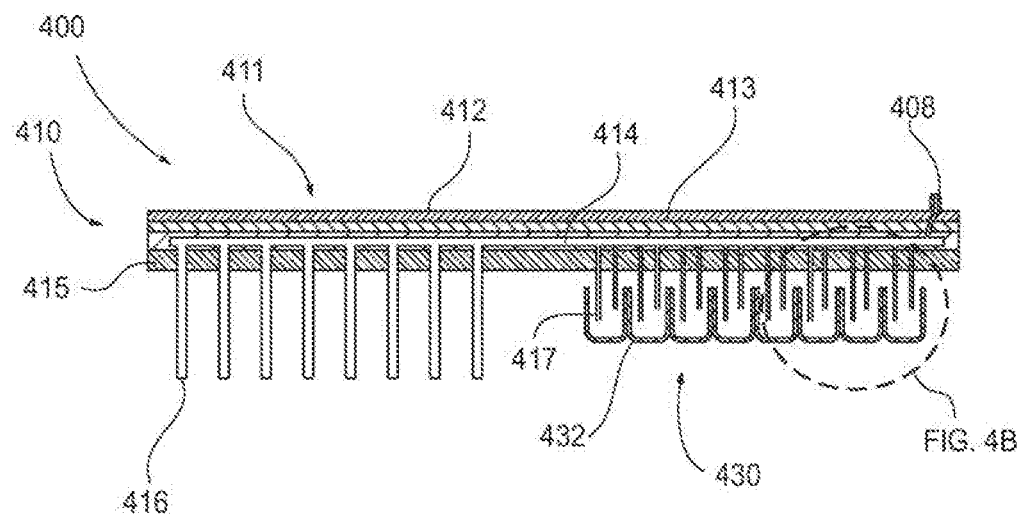
FIG. 4A depicts a schematic view of an illustrative pneumatic lid that incorporates polymer tubes at a destination plate interface according to one, or more embodiments shown and described herein.
Figure 4B:
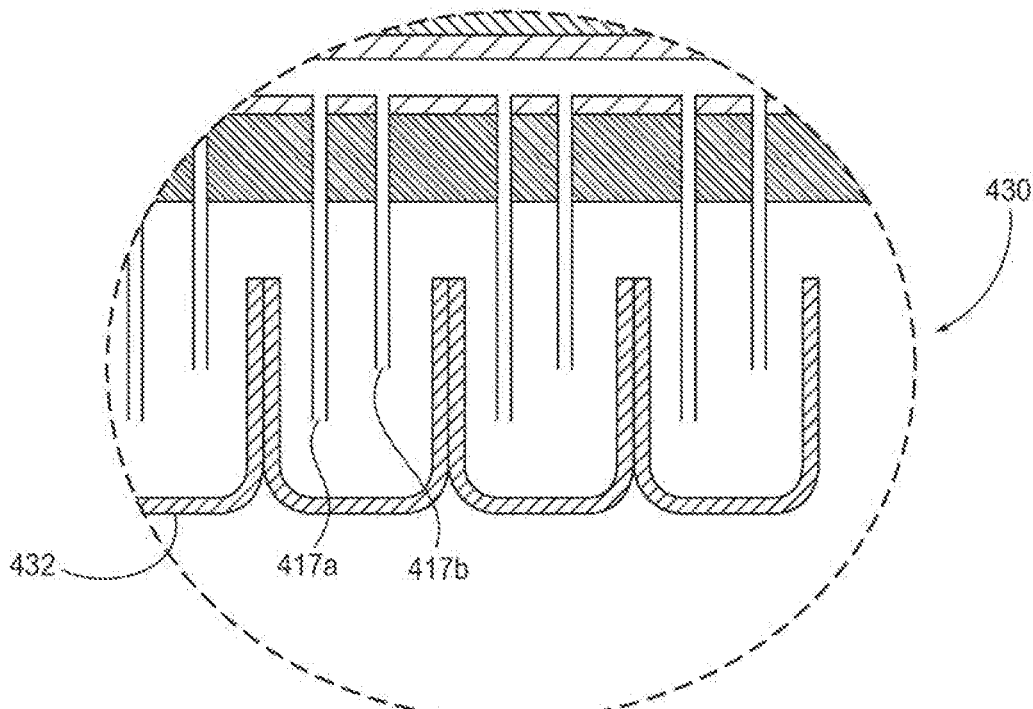
FIG. 4B depicts a detailed view of the polymer tubes of FIG. 4A at the destination plate interface according to one or more embodiments shown and described herein.

FIGS. 4A and 4B depict another embodiment where the apparatus, generally designated 400, incorporates a pneumatic lid 410 having polymer tubes 417 located at an interface with a destination microplate 430. Except as specifically described herein, the various remaining components shown in FIGS. 4A and 4B may be constructed and configured similar to the like-numbered components in FIGS. 1A, 1B, 3A, and 3B. For example, the body 411 depicted in FIG. 4A may be constructed and configured in a manner similar to the body 111 described with respect to FIGS. 1A and 1B and the body 311 described with respect to FIG. 3A. In another example, the first layer 412 depicted in FIG. 4A may be constructed and configured in a manner similar to the top layer 312 described with respect to FIG. 3A.

In the embodiment depicted in FIGS. 4A and 4B, the fluid interface to the destination microplate 430 may be provided via the polymer tubes 417, which are fluidly coupled to microfluidic channels located within a third layer 414. As particularly shown in FIG. 4B, a first tube 417a may provide a fluid inlet into each well 432 of the destination microplate 430 and a second tube 417b may provide a fluid outlet from each well 432 of the destination microplate 430. In some embodiments, the first tube 417a may extend a distance into a respective well 432 that is different from a second distance at which the second tube 417b extends. As such, the various tubes 417 may be located at various heights within each well 432. In some embodiments, each of the various tubes 417 may be controlled by separate valving or common valving, and each of the various tubes 417 may be actuated by pressure or vacuum, as described in greater detail herein.

Use of microfluidic channels in the pneumatic lid as described herein may provide for design flexibility with respect to interfacing particular source wells with particular destination wells. For example as shown in FIGS. 5A-5C, several well-to-well mapping possibilities may exist.

Figure 5C:
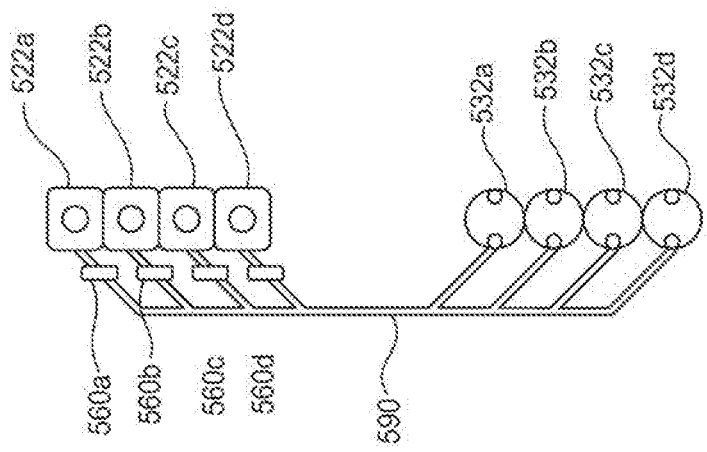
FIG. 5C depicts a schematic view of yet another illustrative pneumatic lid interface well mapping configuration according to one or more embodiments shown and described herein.
Figure 5B:
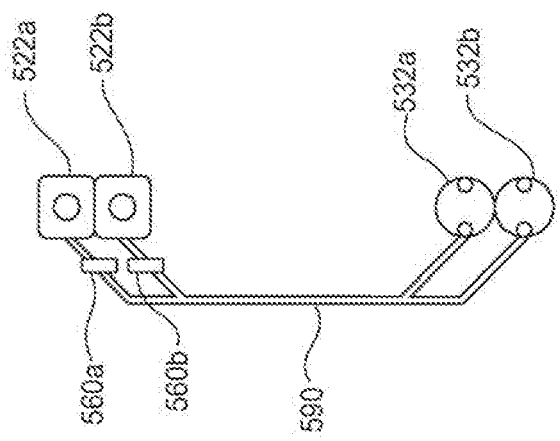
FIG. 5B depicts a schematic view of another illustrative pneumatic lid interface well mapping configuration according to one or more embodiments shown and described herein.
Figure 5A:
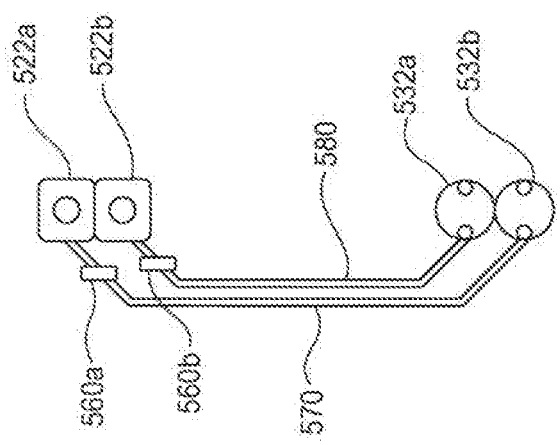
FIG. 5A depicts a schematic view of an illustrative pneumatic lid interface well mapping configuration according to one or more embodiments shown and described herein.

FIG. 5A depicts a direct one to one mapping. As such, each of the source wells 522a, 522b has a corresponding valve 560a, 560b fluidly coupled thereto. Each valve 560a, 560b is fluidly coupled to a corresponding destination well 532a, 532b via a corresponding conduit 570, 580. As such, fluid contained within a first source well 522a is selectively controlled by a first valve 560a to move fluid through a first conduit 570 into a corresponding first destination well 532a. Similarly, fluid contained within a second source well 522b is selectively controlled by a second valve 560*b* to move fluid through a second conduit 580 into a corresponding second destination well 532*b*.

In other embodiments, as shown in FIG. 5B, two source wells may be interfaced to either of two destination wells. More specifically, each of the source wells 522*a*, 522*b* has a corresponding valve 560*a*, 560*b* fluidly coupled thereto. Each valve 560*a*, 560*b* is fluidly coupled to all of a plurality of destination wells 532*a*, 532*b* via a communal conduit 590. As such, fluid contained within a first source well 522*a* is selectively controlled by a first valve 560*a* to move fluid through the communal conduit 590 into a first destination well 532*a* and/or a second destination well 532*b*. Similarly, fluid contained within a second source well 522*b* is selectively controlled by a second valve 560*b* to move fluid through the communal conduit 590 into the first destination well 532*a* and/or the second destination well 532*b*. In this embodiment, a particular destination well can receive more than one reagent, which may offer experimental flexibility as well as redundancy (duplicates).

FIG. 5C depicts an illustrative example of quadruplicate well mapping. FIG. 5C depicts four source wells 522*a*, 522*b*, 522*c*, 522*d* fluidly coupled to a corresponding valve 560*a*, 560*b*, 560*c*, 560*d*, each of which is fluidly coupled to all of a plurality of destination wells 532*a*, 532*b*, 532*c*, 532*d* via a communal conduit 590. The various wells and valves operate in a manner similar to those described with respect to FIG. 5B. In this embodiment, a particular destination well, can receive more than one reagent, which may offer experimental flexibility as well as redundancy (duplicates). Other configurations not specifically described herein may also be possible without departing from the scope of the present disclosure. Also, as previously mentioned herein, active valves may not be used. Rather, the actuation of fluid flow may be accomplished via a separate pressurization of an isolated well pneumatic line from the pneumatic controller. In this instance however, it may be desirable to incorporate a simple passive check valve to prevent back-flow from one source well into another source well in the context of multiple well mapping scenarios as described in FIGS. 5A-5C.

In various embodiments, it may be necessary to ensure that cells contained within destination wells do not experience significant deviations from atmospheric pressure in the process of moving fluids within the apparatus. When it is settled and pressurized as described herein. As such, it may be necessary to introduce pressure differentials (positive or negative) in the source wells and the destination wells without introducing significant (<0.1 atm) deviations from absolute atmospheric pressures in the cell microplate. This may be incorporated in the design of the apparatus and the various components thereof, and in some embodiments may be based on fluid channel geometry, valving, and/or various pressures used at the pneumatic controller.

In various embodiments, waste removal may be necessary to eliminate an artificial condition of extraneous waste build-up at the cell layer, and may be in concordance with the in vivo condition of a steady-state concentration of nutrients and waste as previously described herein. In some embodiments, the volume of material in each well remains constant and the fluid volume removed is equivalent to that which is added. FIGS. 6A and 6B depict illustrative apparatus configurations that are suited for waste removal. For example, as shown in FIG. 6A, waste may be carried out to a waste well 622*b* via one or more conduits 670, 680. In another example, as shown in FIG. 6B, a source well 622*a* may be fluidly coupled to a first valve 650*a*, which controls fluid flow via a first conduit 670 to a first destination well 632*a* and/or a second destination well 632*b*. The waste well 622*b* may be fluidly coupled to a second valve 650*a*, which controls fluid flow via a second conduit 680 to the first destination well 632*a* and/or the second destination well 632*b*. In such an embodiment, the source well 622*a* may be left empty at the beginning of an experiment and subsequently used as a waste collection vessel. This may be useful in situations where it may be desirable to keep the perfusion waste from various wells for subsequent (e.g., biochemical) analysis. In some embodiments, the timing and volumes of adding to the wells and the related timing and volumes of waste extraction may be varied to take advantage of other factors such as convection, diffusional mixing, and/or the like.

It should be appreciated that methods of assembling the various apparatuses described hereinabove may include various steps such as, but not limited to, providing the microplates and placing the pneumatic lid over the microplates (including placing the portions of the pneumatic lid and the corresponding bridge portion). It should further be appreciated that methods may include inserting extension pieces into the wells of the corresponding microplates to fluidly couple the microplates to one another. The lid may be coupled via a non-mechanical device, as described herein. In addition, a differential pressure may be activated to control fluid flow.

It should now be understood that the systems, apparatuses, and methods described herein incorporate a pneumatic lid with traditional microplate components for the purposes of simulating in vivo conditions for cellular cultures. The systems, apparatuses, and methods described herein use traditional microplate technology, such that it can be used with current work flow and readout technologies. Moreover, use of traditional microplate technology eliminates difficulty with seeding cells in microfluidic channel devices. The systems, apparatuses, and methods described herein provide a capacity for a greater experimental throughput relative to other technologies, an ability to control dissolved gas composition of the cell culture media (e.g., oxygen composition), an ability to form a solvent-free, non-breathing bond, which results in a closed design that eliminates evaporation and resulting edge effects associated with other microplate cultures, a device that is capable of integrated perfusion while simultaneously being accessible to microscopic imaging, allows for independent well control (ability to perfuse individual wells, groups of wells, or all wells in unison), ability to use active flow whereby flow rate and flow duration can be controlled by the user, ability to provide an enhanced experimental duration for a given flow rate via a deep well source microplate, and/or an apparatus that eliminates or minimizes the use of PDMS material, instead incorporating materials such as SEBS to provide enhanced chemical resistance and/or gas permeability.

EXAMPLES

Illustrative examples of potential uses of the systems, apparatuses, and methods described above are provided below. Such examples are merely illustrative in nature and are not intended to limit the scope of the present disclosure. In addition, the list of illustrative examples provided below is not exhaustive and may include other examples without departing from the scope of the present disclosure.

Such a device or technique could be used to feed cells in an automated manner, using more physiological concentrations of nutrients while simultaneously achieving a more biologically relevant, steady-state concentration of nutrients and waste products. As described, this method would benefit almost all known in vitro cell models and would be applicable in broad fields of life science research including drug discovery and safety testing.

Such a device or technique could be used to discover, design, and validate media formulations which are more consistent with physiological conditions.

Such a device or technique could be used to more easily investigate and optimize the timing and composition of media constituents in studying stem cell differentiation.

Such a device or technique could be used to more easily investigate the effects of gas composition, e.g., oxygen concentration on various in vitro cell models such as neurons or hepatocytes.

Such a device or technique could be used to add a cell modulating reagent while simultaneously imaging the cells (e.g., acute drug exposure studies)

Such a device or technique could be used to add drugs or other cell modulators via the media in a manner which is more physiological in delivery and less perturbing to the cultures than removing the plate from the incubator.

Such a device or technique could be used to change media constituents from reagent A to reagent B, and/or remove a drug or media constituent (wash-out) from the culture.

Such a device or technique could be used to mimic or model the drug metabolism and pharmokinetic concentration profile of a drug, agent or metabolite by automatically changing the concentration of the agent over time.

Such a device or technique could be used to sample waste products from the cells for further analysis.

Such a device or technique which would allow for perfusion of one well, arbitrary groups of wells, or all the wells of a standard microplate.

Such a device or technique where the pneumatic lid assembly is packaged as a sterile consumable and applicable to sterile cell culture techniques.

Item List

Item 1. A pneumatic lid comprising:
a body comprising one or more microfluidic channels, wherein at least a portion of the body is constructed of styrene ethylene butylene styrene (SEBS);
one or more first extension pieces fluidly coupled to the one or more microfluidic channels and extending from the body; and
one or more second extension pieces fluidly coupled to the one or more microfluidic channels and extending from the body.

Item 2. A pneumatic lid comprising:
a first portion comprising one or more first microfluidic channels that are configured to be fluidly coupled to one or more first wells;
a second portion comprising one or more second microfluidic channels that are configured to be fluidly coupled to one or more second wells that are separate from the one or more first wells; and
a removable bridge portion extending between the first portion and the second portion, wherein the removable bridge portion, when coupled to the first portion and the second portion, fluidly couples the one or more first microfluidic channels to the one or more second microfluidic channels,
wherein the first portion and the second portion, when coupled to the one or more first wells and the one or more second wells, respectively provide an airtight seal over the one or more first wells and the one or more second wells.

Item 3. The pneumatic lid of item 2, wherein the pneumatic lid is constructed of styrene ethylene butylene styrene (SEBS).

Item 4. The pneumatic lid of item 1 or 2, wherein the first portion and the second portion, when coupled to the one or more first wells and the one or more second wells, respectively provide the airtight seal over the one or more first wells and the one or more second wells via a non-mechanical device.

Item 5. The pneumatic lid of any one of items 2 to 4, further comprising one or more valves that selectively control fluid flow within the one or more microfluidic channels.

Item 6. The pneumatic lid of any one of items 2 to 5, wherein a fluid flow rate and a duration are controlled by activation of a differential pressure.

Item 7. The pneumatic lid of any one of items 2 to 6, wherein the airtight seal is a reversible airtight seal.

Item 8. The pneumatic lid of any of items 2 to 7, further comprising one or more pneumatic control fittings fluidly coupled to at least a portion of the pneumatic lid.

Item 9. An apparatus comprising:
a first microplate having a first open portion and defining one or more first wells therein;
a second microplate having a second open portion and defining one or more second wells therein; and
a pneumatic lid constructed of styrene ethylene, butylene styrene (SEBS), the pneumatic lid extending over the first open portion and the second open portion and comprising one or more microfluidic channels that fluidly couple the one or more first wells to the one or more second wells, wherein the pneumatic lid provides an airtight seal over the first microplate and the second microplate.

Item 10. An apparatus comprising:
a first microplate having a first open portion and defining one or more first wells therein;
a second microplate having a second open portion and defining one or more second wells therein; and
a pneumatic lid extending over the first open portion and the second open portion, the pneumatic lid comprising one or more microfluidic channels that fluidly couple the one or more first wells to the one or more second wells, wherein the pneumatic lid provides an airtight seal over the first microplate and the second microplate.

Item 11. An apparatus comprising:
a first microplate having a first open portion and defining one or more first wells therein;
a second microplate having a second open portion and defining one or more second wells therein; and
a pneumatic lid comprising:
a first portion extending over the first open portion, the first portion comprising one or more first microfluidic channels that are fluidly coupled to the one or more first wells,
a second portion extending over the second open portion, the second portion comprising one or more second microfluidic channels that are fluidly coupled to the one or more second wells, and
a removable bridge portion extending between the first portion and the second portion, wherein the removable bridge portion, when coupled to the first portion and the second portion, fluidly couples the one or more first microfluidic channels to the one or more second microfluidic channels,
wherein the pneumatic lid provides an airtight seal over the first microplate and the second microplate.

Item 12. The apparatus of item 10 or item 11, wherein the pneumatic lid is constructed of a thermoplastic elastomer that forms a reversible and gas impermeable bond with the first microplate and the second microplate.

Item 13. The apparatus of item 12, wherein the thermoplastic elastomer is styrene ethylene butylene styrene (SEBS).

Item 14. The apparatus of any one of items 9-13, wherein the pneumatic lid further comprises:
one or more first extension pieces extending into the one or more first wells of the first microplate; and
one or more second extension pieces extending into the one or more second wells of the second microplate,
wherein the one or more microfluidic channels fluidly couple the one or more first extension pieces to the one or more second extension pieces.

Item 15. The apparatus of any one of items 9-13, wherein the pneumatic lid further comprises:
one or more extension pieces extending into the one or more first wells of the first microplate; and
one or more polymer plugs extending into the one or more second wells of the second microplate, each one of the one or more polymer plugs comprising one or more bores therein,
wherein the one or more microfluidic channels fluidly couple the one or more extension pieces to the one or more bores.

Item 16. The apparatus of any one of items 9, 10, or 12 to 15 wherein the pneumatic lid comprises:
a first portion extending over the first open portion, the first portion comprising one or more first microfluidic channels that are fluidly coupled to the one or more first wells,
a second portion extending over the second open portion, the second portion comprising one or more second microfluidic channels that are fluidly coupled to the one or more second wells, and
a removable bridge portion extending between the first portion and the second portion, wherein the removable bridge portion, when coupled to the first portion and the second portion, fluidly couples the one or more first microfluidic channels to the one or more second microfluidic channels.

Item 17. The apparatus of any one of items 9-16, wherein the first microplate does not contact the second microplate.

Item 18. The apparatus of any one of items 9-17, wherein the pneumatic lid is coupled to the first microplate and the second microplate via a non-mechanical device.

Item 19. The apparatus of any one of items 9-18, further comprising one or more valves that selectively control fluid flow within the one or more microfluidic channels.

Item 20. The apparatus of any one of items 9-19, wherein a fluid flow rate and a duration are controlled by activation of a differential pressure.

Item 21. The apparatus of any one of items 9-20, wherein the airtight seal is a reversible airtight seal.

Item 22. The apparatus of any one of items 9-21, further comprising one or more pneumatic control fitting fluidly coupled to at least a portion of the pneumatic lid.

Item 23. The apparatus of item any one of items 9-22, wherein:
the pneumatic lid further comprises a thermoplastic elastomer layer; and
the airtight seal is created via the thermoplastic elastomer layer.

Item 24. The apparatus of any one of items 9-23, wherein at least one of the first microplate and the second microplate comprises a deep well plate having a height greater than 1 cm.

Item 25. A method of constructing an apparatus for transferring fluid, the method comprising:
providing a first microplate having a first open portion and defining one or more first wells therein;
providing a second microplate having a second open portion and defining one or more second wells therein; and
placing a pneumatic lid constructed of styrene ethylene butylene styrene (SEBS) over the first open portion and the second open portion such that one or more microfluidic channels within the pneumatic lid are fluidly coupled to the one or more first wells and the one or more second wells, wherein the pneumatic lid provides an airtight seal over the first microplate and the second microplate.

Item 26. The method of item 25, wherein placing the pneumatic lid comprises:
inserting one or more first extension pieces into the one or more first wells of the first microplate; and
inserting one or more second extension pieces into the one or more second wells of the second microplate,
wherein the one or more microfluidic channels fluidly couple the one or more first extension pieces to the one or more second extension pieces.

Item 27. A method of constructing an apparatus for transferring fluid, the method comprising:
providing a first microplate having a first open portion and defining one or more first wells therein;
providing a second microplate having a second open portion and defining one or more second wells therein;
placing a first portion of a pneumatic lid over the first open portion such that one or more first microfluidic channels within the first portion are fluidly coupled to the one or more first wells;
placing a second portion of a pneumatic lid over the second open portion such that one or more second microfluidic channels within the second portion are fluidly coupled to the one or more second wells; and
placing a removable bridge portion between the first portion and the second portion of the pneumatic lid to fluidly couple the one or more first microfluidic channels to the one or more second microfluidic channels.

Item 28. The method of item 27, wherein:
placing the first portion of the pneumatic lid comprises inserting one or more first extension pieces into the one or more first wells of the first microplate; and
placing the second portion of the pneumatic lid comprises inserting one or more second extension pieces into the one or more second wells of the second microplate.

Item 29. The method of any one of items 25-28, wherein placing the second microplate comprises placing the second microplate at a distance from the first microplate such that the second microplate does not contact the first microplate.

Item 30. The method of any one of items 25-29, wherein placing the pneumatic lid, or a portion thereof, comprises coupling the pneumatic lid to the first microplate and the second microplate via a non-mechanical device.

Item 31. The method of any one of items 25-30, further comprising activating a differential pressure to control fluid flow within the one or more microfluidic channels.

Item 32. A system for transferring fluid, the system comprising:
a first microplate having a first open portion and defining one or more first wells therein;
a second microplate that is separate from the first microplate, the second microplate having a second open portion and defining one or more second wells therein;
a pneumatic lid constructed of styrene ethylene butylene styrene (SEBS) which forms a reversible and gas impermeable bond with the first microplate and the second microplate, the pneumatic lid comprising:
a first portion extending over the first open portion, the first portion comprising one or more first extension pieces extending into the one or more first wells of the first microplate and one or more first microfluidic channels that are fluidly coupled to the one or more first wells via the one or more first extension pieces,
a second portion extending over the second, open portion, the second portion comprising one or more second extension pieces extending into the one, or more second wells of the second microplate and one or more second microfluidic channels that are fluidly coupled to the one or more second wells via the one or more second microfluidic channels, and
a removable bridge portion extending between the first portion and the second portion, wherein the removable bridge portion, when coupled to the first portion and the second portion, fluidly couples the one or more first microfluidic channels to the one or more second microfluidic channels; and
one or more valves fluidly coupled to the pneumatic lid, the one or more valves configured to selectively control fluid flow within the one or more first microfluidic channels and the one or more second microfluidic channels,
wherein the fluid is transferred between the first microplate and the second microplate via the pneumatic lid and the one or more valves.

Item 33. An apparatus for transferring fluid from a first standard microplate to a second standard microplate according to one or more of the embodiments described herein.

Item 34. A system for transferring fluid from a first standard microplate to a second standard microplate according to one or more of the embodiments described herein.

Item 35. A method for transferring fluid from a first standard microplate to a second standard microplate according to one or more of the embodiments described herein.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A pneumatic lid comprising:
A) a body comprising one or more microfluidic channels, wherein at least a portion of the body is constructed of styrene ethylene butylene styrene (SEBS);
one or more first extension pieces fluidly coupled to the one or more microfluidic channels and extending from the body; and
one or more second extension pieces fluidly coupled to the one or more microfluidic channels and extending from the body, wherein the one or more second extension pieces are further fluidly coupled to the one more first extension pieces via the one or more microfluidic channels; or
(B) a first portion comprising one or more first microfluidic channels that are configured to be fluidly coupled to one or more first wells;
a second portion comprising one or more second microfluidic channels that are configured to be fluidly coupled to one or more second wells that are separate from the one or more first wells; and
a removable bridge portion extending between the first portion and the second portion, wherein the removable bridge portion, when coupled to the first portion and the second portion, fluidly couples the one or more first microfluidic channels to the one or more second microfluidic channels,
wherein the first portion and the second portion, when coupled to the one or more first wells and the one or more second wells, respectively provide an airtight seal over the one or more first wells and the one or more second wells.

2. The pneumatic lid of claim 1, wherein the pneumatic lid comprises option (B), and wherein the first portion and the second portion, when coupled to the one or more first wells and the one or more second wells, respectively provide the airtight seal over the one or more first wells and the one or more second wells via a non-mechanical device.

3. The pneumatic lid of claim 1, further comprising one or more valves that selectively control fluid flow within the one or more microfluidic channels.

4. The pneumatic lid of claim 1, wherein a fluid flow rate and a duration are controlled by activation of a differential pressure.

5. The pneumatic lid of claim 1, wherein the pneumatic lid comprises option (B), and wherein the airtight seal is a reversible airtight seal.

6. The pneumatic lid of claim 1, further comprising one or more pneumatic control fittings fluidly coupled to at least a portion of the pneumatic lid.

7. An apparatus comprising:
(A) a first microplate having a first open portion and defining one or more first wells therein;
a second microplate having a second open portion and defining one or more second wells therein; and
a pneumatic lid constructed of styrene ethylene butylene styrene (SEBS), the pneumatic lid positioned on top of the first microplate and the second microplate such that the pneumatic lid extends over the first open portion and the second open portion, the pneumatic lid comprising one or more microfluidic channels that fluidly couple the one or more first wells to the one or more second wells when the pneumatic lid is positioned over the first open portion and the second open portion, wherein the pneumatic lid provides an airtight seal over the first microplate and the second microplate; or
(B) a first microplate having a first open portion and defining one or more first wells therein;
a second microplate having a second open portion and defining one or more second wells therein; and
a pneumatic lid positioned on top of the first microplate and the second microplate such that the pneumatic lid extends over the first open portion and the second open portion, the pneumatic lid comprising one or more microfluidic channels that fluidly couple the one or more first wells to the one or more second wells when the pneumatic lid is positioned over the first open portion and the second open portion, wherein the pneumatic lid provides an airtight seal over the first microplate and the second microplate; or
(C) a first microplate having a first open portion and defining one or more first wells therein;
a second microplate having a second open portion and defining one or more second wells therein; and
a pneumatic lid comprising:

a first portion extending over the first open portion, the first portion comprising one or more first microfluidic channels that are fluidly coupled to the one or more first wells, a second portion extending over the second open portion, the second portion comprising one or more second microfluidic channels that are fluidly coupled to the one or more second wells, and a removable bridge portion extending between the first portion and the second portion, wherein the removable bridge portion, when coupled to the first portion and the second portion, fluidly couples the one or more first microfluidic channels to the one or more second microfluidic channels, wherein the pneumatic lid provides an airtight seal over the first microplate and the second microplate.

8. The apparatus of claim 7, wherein the pneumatic lid is constructed of a thermoplastic elastomer that forms a reversible and gas impermeable bond with the first microplate and the second microplate.

9. The apparatus of claim 8, wherein the thermoplastic elastomer is styrene ethylene butylene styrene (SEBS).

10. The apparatus of claim 7, wherein the pneumatic lid further comprises:
one or more first extension pieces extending into the one or more first wells of the first microplate; and
one or more second extension pieces extending into the one or more second wells of the second microplate,
wherein the one or more microfluidic channels fluidly couple the one or more first extension pieces to the one or more second extension pieces.

11. The apparatus of claim 7, wherein the pneumatic lid further comprises:
one or more extension pieces extending into the one or more first wells of the first microplate; and
one or more polymer plugs extending into the one or more second wells of the second microplate, each one of the one or more polymer plugs comprising one or more bores therein,
wherein the one or more microfluidic channels fluidly couple the one or more extension pieces to the one or more bores.

12. The apparatus of claim 7, wherein the pneumatic lid comprises:
a first portion extending over the first open portion, the first portion comprising one or more first microfluidic channels that are fluidly coupled to the one or more first wells,
a second portion extending over the second open portion, the second portion comprising one or more second microfluidic channels that are fluidly coupled to the one or more second wells, and
a removable bridge portion extending between the first portion and the second portion, wherein the removable bridge portion, when coupled to the first portion and the second portion, fluidly couples the one or more first microfluidic channels to the one or more second microfluidic channels.

13. The apparatus of claim 7, wherein the first microplate does not contact the second microplate.

14. The apparatus of claim 7, wherein the pneumatic lid is coupled to the first microplate and the second microplate via a non-mechanical device.

15. The apparatus of claim 7, further comprising one or more valves that selectively control fluid flow within the one or more microfluidic channels.

16. The apparatus of claim 7, wherein a fluid flow rate and a duration are controlled by activation of a differential pressure.

17. The apparatus of claim 7, wherein the airtight seal is a reversible airtight seal.

18. The apparatus of claim 7, further comprising one or more pneumatic control fittings fluidly coupled to at least a portion of the pneumatic lid.

19. The apparatus of claim 7, wherein:
the pneumatic lid further comprises a thermoplastic elastomer layer; and
the airtight seal is created via the thermoplastic elastomer layer.

20. The apparatus of claim 7, wherein at least one of the first microplate and the second microplate comprises a deep well plate having a height greater than 1 cm.

21. A method of constructing an apparatus for transferring fluid, the method comprising:
(A) providing a first microplate having a first open portion and defining one or more first wells therein;
providing a second microplate having a second open portion and defining one or more second wells therein; and
placing a pneumatic lid constructed of styrene ethylene butylene styrene (SEBS) on top of the first microplate and the second microplate such that the pneumatic lid extends over the first open portion and the second open portion such that one or more microfluidic channels within the pneumatic lid are fluidly coupled to the one or more first wells and the one or more second wells when the pneumatic lid is positioned over the first open portion and the second open portion,
wherein the pneumatic lid provides an airtight seal over the first microplate and the second microplate; or
(B) providing a first microplate having a first open portion and defining one or more first wells therein;
providing a second microplate having a second open portion and defining one or more second wells therein;
placing a first portion of a pneumatic lid over the first open portion such that one or more first microfluidic channels within the first portion are fluidly coupled to the one or more first wells;
placing a second portion of a pneumatic lid over the second open portion such that one or more second microfluidic channels within the second portion are fluidly coupled to the one or more second wells; and
placing a removable bridge portion between the first portion and the second portion of the pneumatic lid to fluidly couple the one or more first microfluidic channels to the one or more second microfluidic channels.

22. The method of claim 21, wherein the method comprises option (A), and wherein placing the pneumatic lid comprises:
inserting one or more first extension pieces into the one or more first wells of the first microplate; and
inserting one or more second extension pieces into the one or more second wells of the second microplate,
wherein the one or more microfluidic channels fluidly couple the one or more first extension pieces to the one or more second extension pieces.

23. The method of claim 21, wherein the method comprises option (B), and wherein:
placing the first portion of the pneumatic lid comprises inserting one or more first extension pieces into the one or more first wells of the first microplate; and placing the second portion of the pneumatic lid comprises inserting one or more second extension pieces into the one or more second wells of the second microplate.

24. The method of claim 21, wherein placing the second microplate comprises placing the second microplate at a distance from the first microplate such that the second microplate does not contact the first microplate.

25. The method of claim 21, wherein placing the pneumatic lid, or a portion thereof, comprises coupling the pneumatic lid to the first microplate and the second microplate via a non-mechanical device.

26. The method of claim 21, further comprising activating a differential pressure to control fluid flow within the one or more microfluidic channels.

27. A system for transferring fluid, the system comprising:
a first microplate having a first open portion and defining one or more first wells therein;
a second microplate that is separate from the first microplate, the second microplate having a second open portion and defining one or more second wells therein;
a pneumatic lid constructed of styrene ethylene butylene styrene (SEBS) which forms a reversible and gas impermeable bond with the first microplate and the second microplate, the pneumatic lid comprising:
a first portion extending over the first open portion, the first portion comprising one or more first extension pieces extending into the one or more first wells of the first microplate and one or more first microfluidic channels that are fluidly coupled to the one or more first wells via the one or more first extension pieces,
a second portion extending over the second open portion, the second portion comprising one or more second extension pieces extending into the one or more second wells of the second microplate and one or more second microfluidic channels that are fluidly coupled to the one or more second wells via the one or more second microfluidic channels, and
a removable bridge portion extending between the first portion and the second portion, wherein the removable bridge portion, when coupled to the first portion and the second portion, fluidly couples the one or more first microfluidic channels to the one or more second microfluidic channels; and
one or more valves fluidly coupled to the pneumatic lid, the one or more valves configured to selectively control fluid flow within the one or more first microfluidic channels and the one or more second microfluidic channels,
wherein the fluid is transferred between the first microplate and the second microplate via the pneumatic lid and the one or more valves.

* * * * *